US009161756B2

(12) United States Patent
Sargeant et al.

(10) Patent No.: US 9,161,756 B2
(45) Date of Patent: Oct. 20, 2015

(54) CLOSURE TAPE DISPENSER

(71) Applicant: Covidien LP, Mansfield, MA (US)

(72) Inventors: Timothy Sargeant, Guilford, CT (US); Frank Viola, Sandy Hook, CT (US); Kevin Condrin, Madison, CT (US)

(73) Assignee: Covidien LP, Mansfield, MA (US)

( * ) Notice: Subject to any disclaimer, the term of this patent is extended or adjusted under 35 U.S.C. 154(b) by 368 days.

(21) Appl. No.: 13/778,847

(22) Filed: Feb. 27, 2013

(65) Prior Publication Data

US 2013/0245680 A1 Sep. 19, 2013

Related U.S. Application Data

(60) Provisional application No. 61/611,722, filed on Mar. 16, 2012.

(51) Int. Cl.
*A61B 17/08* (2006.01)
*A61B 17/00* (2006.01)
*A61F 13/15* (2006.01)
*A61F 13/36* (2006.01)
*A61F 13/45* (2006.01)
*A61F 13/00* (2006.01)

(52) U.S. Cl.
CPC ........... *A61B 17/085* (2013.01); *A61B 17/0057* (2013.01); *A61F 13/15* (2013.01); *A61F 13/36* (2013.01); *A61F 13/45* (2013.01); *A61B 2017/0065* (2013.01); *A61B 2017/00637* (2013.01); *A61F 2013/0054* (2013.01)

(58) Field of Classification Search
CPC ................. A61B 17/08; A61B 17/085; A61B 2017/0065
See application file for complete search history.

(56) References Cited

U.S. PATENT DOCUMENTS

| 3,991,754 | A | * | 11/1976 | Gertzman ..................... 604/387 |
| 4,359,049 | A | | 11/1982 | Brummer et al. |
| 4,447,482 | A | * | 5/1984 | Heinzelman et al. ........ 428/42.3 |
| 4,874,368 | A | | 10/1989 | Miller et al. |
| 4,978,336 | A | | 12/1990 | Capozzi et al. |
| 4,979,942 | A | | 12/1990 | Wolf et al. |
| 5,259,835 | A | * | 11/1993 | Clark et al. ..................... 602/48 |
| 5,263,927 | A | | 11/1993 | Shlain |
| 5,368,563 | A | | 11/1994 | Lonneman et al. |
| 5,645,566 | A | * | 7/1997 | Brenneman et al. .......... 606/213 |

(Continued)

FOREIGN PATENT DOCUMENTS

| EP | 2359782 A1 | 8/2011 |
| EP | 2361567 A1 | 8/2011 |

(Continued)

OTHER PUBLICATIONS

European Search Report EP13159340 dated Aug. 1, 2014.

(Continued)

*Primary Examiner* — Jonathan W Miles

(57) ABSTRACT

A surgical tape applicator includes a dispenser housing, a protective liner, and a surgical tape. The dispenser housing has a proximal end and a distal end and defines a passageway therethrough. The protective liner is disposed within the passageway of the housing. The surgical tape is at least partially disposed within the dispenser housing and protected by the protective liner. The surgical tape has a first surface and a second surface each having at least one tissue reactive component.

14 Claims, 6 Drawing Sheets

(56) References Cited

U.S. PATENT DOCUMENTS

| | | | |
|---|---|---|---|
| 5,653,730 A * | 8/1997 | Hammerslag | 606/214 |
| 5,941,898 A * | 8/1999 | Moenning et al. | 606/213 |
| 6,126,675 A * | 10/2000 | Shchervinsky et al. | 606/213 |
| 6,333,051 B1 | 12/2001 | Kabanov et al. | |
| 6,416,506 B1 | 7/2002 | Tilton, Jr. et al. | |
| 6,527,749 B1 | 3/2003 | Roby et al. | |
| 6,632,929 B1 | 10/2003 | Wilchek et al. | |
| 6,638,508 B2 | 10/2003 | Schechter et al. | |
| 6,648,922 B2 | 11/2003 | Ung-Chhun et al. | |
| 6,981,983 B1 * | 1/2006 | Rosenblatt et al. | 606/216 |
| 7,044,982 B2 * | 5/2006 | Milbocker | 623/23.72 |
| 7,074,294 B2 * | 7/2006 | Dubrow | 156/276 |
| 7,699,191 B2 | 4/2010 | Sheets, Jr. et al. | |
| 7,858,079 B2 | 12/2010 | Hadba et al. | |
| 8,992,567 B1 * | 3/2015 | Houser | 606/213 |
| 9,060,767 B2 * | 6/2015 | Bonutti | 1/1 |
| 2001/0018598 A1 * | 8/2001 | Cruise et al. | 606/214 |
| 2001/0044637 A1 * | 11/2001 | Jacobs et al. | 606/221 |
| 2002/0022266 A1 | 2/2002 | Wagner et al. | |
| 2002/0072767 A1 * | 6/2002 | Zhu | 606/213 |
| 2002/0077661 A1 * | 6/2002 | Saadat | 606/221 |
| 2002/0128234 A1 | 9/2002 | Hubbell et al. | |
| 2002/0128672 A1 * | 9/2002 | Dinger et al. | 606/153 |
| 2003/0022216 A1 | 1/2003 | Mao et al. | |
| 2003/0050590 A1 * | 3/2003 | Kirsch | 602/52 |
| 2003/0153001 A1 | 8/2003 | Soane et al. | |
| 2003/0181423 A1 | 9/2003 | Clapper et al. | |
| 2004/0023413 A1 | 2/2004 | Opalsky | |
| 2004/0049207 A1 * | 3/2004 | Goldfarb et al. | 606/139 |
| 2004/0193113 A1 | 9/2004 | Gillis et al. | |
| 2004/0215231 A1 * | 10/2004 | Fortune et al. | 606/213 |
| 2004/0220591 A1 * | 11/2004 | Bonutti | 606/151 |
| 2004/0254594 A1 * | 12/2004 | Alfaro | 606/151 |
| 2005/0119613 A1 | 6/2005 | Moenning et al. | |
| 2005/0153090 A1 | 7/2005 | Marchitto et al. | |
| 2005/0177144 A1 * | 8/2005 | Phan et al. | 606/14 |
| 2005/0182443 A1 * | 8/2005 | Jonn et al. | 606/213 |
| 2005/0192654 A1 * | 9/2005 | Chanduszko et al. | 607/116 |
| 2005/0244453 A1 | 11/2005 | Stucke et al. | |
| 2005/0281802 A1 | 12/2005 | Gong et al. | |
| 2005/0283189 A1 * | 12/2005 | Rosenblatt | 606/216 |
| 2006/0004407 A1 * | 1/2006 | Hiles et al. | 606/215 |
| 2006/0025815 A1 | 2/2006 | McGurk et al. | |
| 2006/0047313 A1 * | 3/2006 | Khanna et al. | 606/232 |
| 2006/0100664 A1 * | 5/2006 | Pai et al. | 606/214 |
| 2007/0073248 A1 | 3/2007 | Moenning | |
| 2007/0282373 A1 * | 12/2007 | Ashby et al. | 606/213 |
| 2008/0114469 A1 * | 5/2008 | O'Brien et al. | 623/23.76 |
| 2008/0221628 A1 | 9/2008 | Milbocker et al. | |
| 2008/0302487 A1 | 12/2008 | Goodman et al. | |
| 2009/0206141 A1 * | 8/2009 | Huitema et al. | 227/176.1 |
| 2010/0087854 A1 * | 4/2010 | Stopek et al. | 606/215 |
| 2010/0285088 A1 | 11/2010 | Sargeant et al. | |
| 2011/0060362 A1 * | 3/2011 | Patel et al. | 606/215 |
| 2011/0270301 A1 * | 11/2011 | Cornet et al. | 606/213 |
| 2012/0172926 A1 * | 7/2012 | Hotter | 606/213 |
| 2012/0191132 A1 * | 7/2012 | Sargeant | 606/214 |

FOREIGN PATENT DOCUMENTS

| | | |
|---|---|---|
| WO | WO94/23759 A1 | 10/1994 |
| WO | WO01/06829 A2 | 2/2001 |
| WO | 01/85077 A1 | 11/2001 |
| WO | WO03/000234 | 1/2003 |
| WO | WO2006/063249 A2 | 6/2006 |
| WO | WO2007/100882 A2 | 9/2007 |
| WO | WO2011/011347 A2 | 1/2011 |

OTHER PUBLICATIONS

European Search Report EP13159339 dated Aug. 1, 2014.
Huang et al., "Biotin-Derivatized Poly (L-lysine)-g-poly(ethylene glycol): A Novel Polymeric Interface for Bioaffinity Sensing" Laboratory for Surface Science and Technology, Department of Materials (2001) pp. 220-230.
Pardridge et al., Pharm. Res. vol. 15, No. 4, 576-582 (1998).
Jia, Z. et al., "Functional Disulfide-Stabilized Polymer-Protein Particles", *Biomacromolecules*, vol. 10, pp. 3253-3258 (2009).
Salmaso et al. Biochim. Biophys. Acta 1726, 57-66 (2005), available on line May 16, 2005.
Xie et al. Design of Attachment Type of Drug Delivery System by Complex Formation of Avidin With Biotinyl Drug Model and Biotinyl Saccharide, QActa Biomaterialia, 1, 2005, pp. 635-641.
European Search Report EP 07751965.0 dated Aug. 27, 2012.
International Search Report from corresponding EP Appln. No. 12192946.7 mailed Feb. 1, 2013.

* cited by examiner

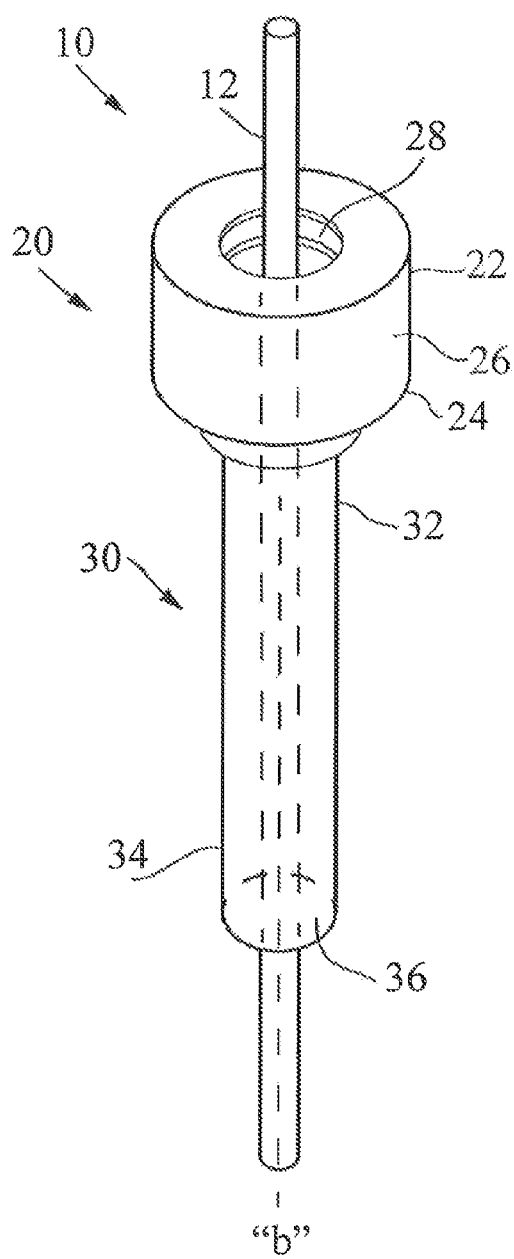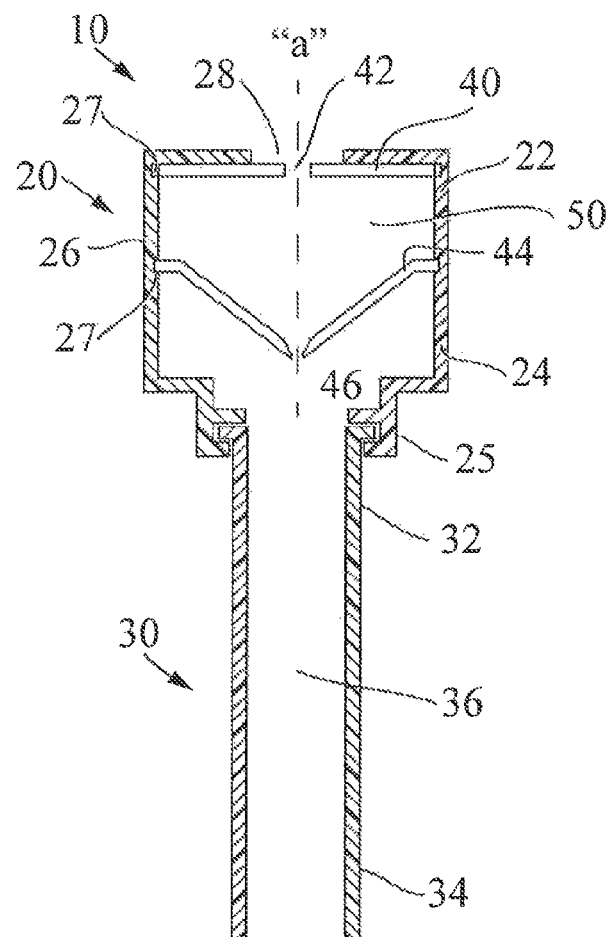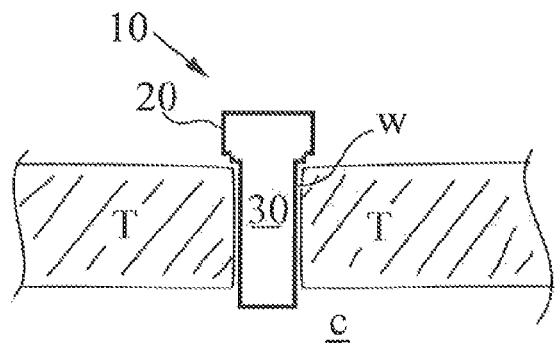
FIG. 1
FIG. 2
FIG. 4

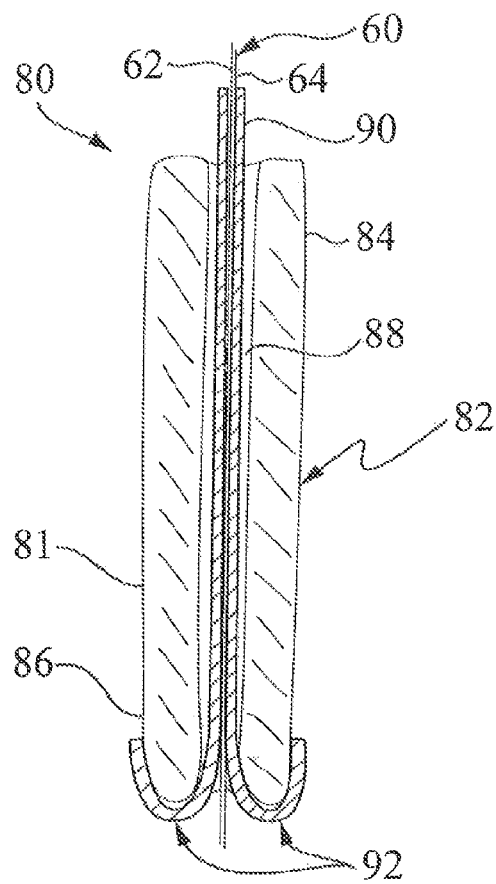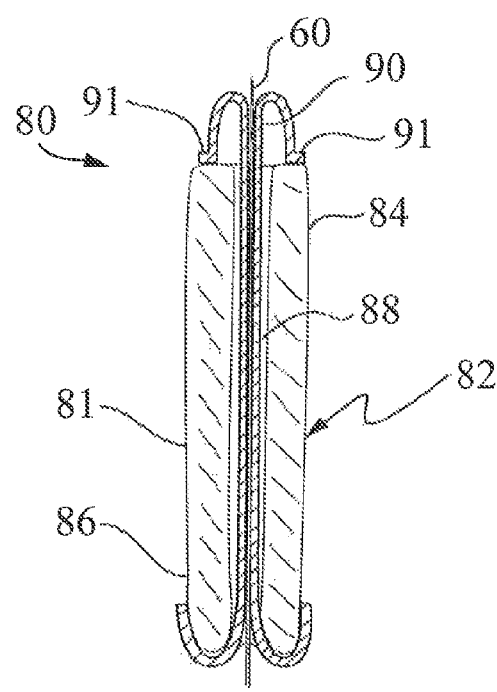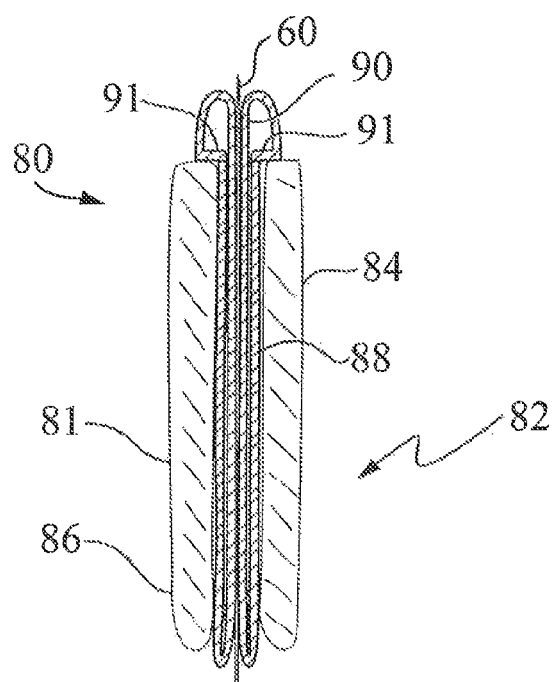
FIG. 3A
FIG. 3B
FIG. 3C

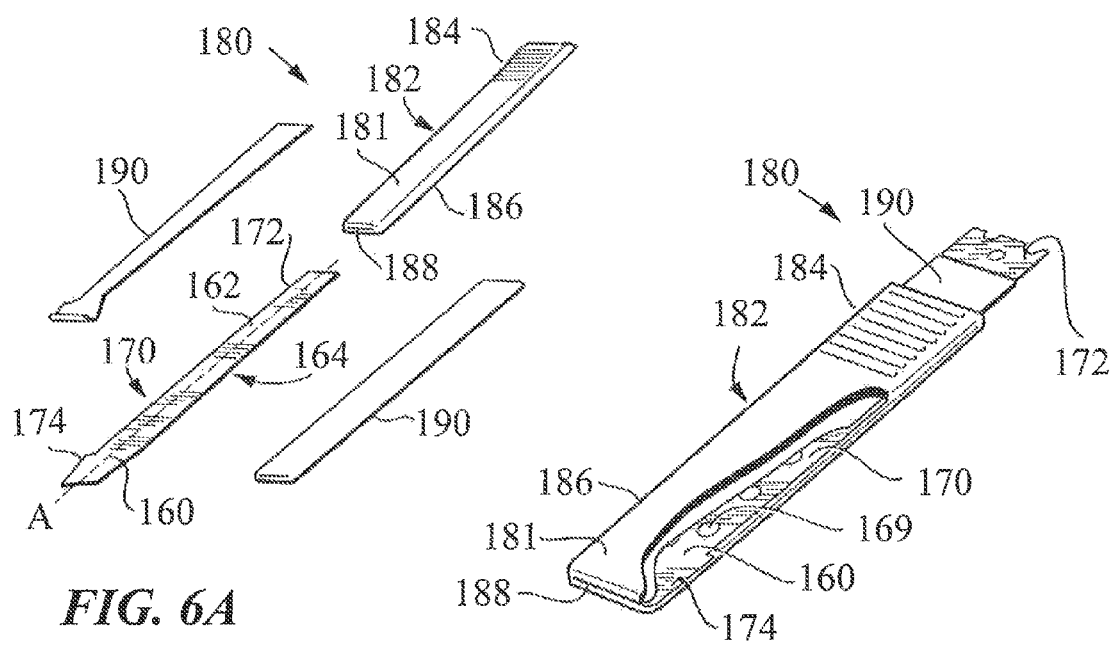
*FIG. 6A*
*FIG. 6B*
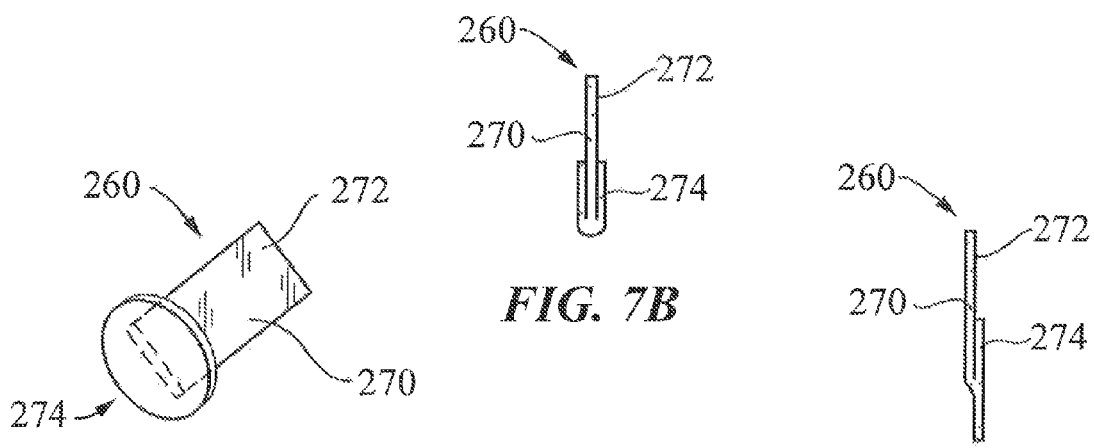
*FIG. 7A*
*FIG. 7B*
*FIG. 7C*

CLOSURE TAPE DISPENSER

CROSS-REFERENCE TO RELATED APPLICATIONS

This application claims the benefit of and priority to U.S. Provisional Patent Application No. 61/611,722, filed Mar. 16, 2012, the entire disclosure of which is incorporated by reference herein.

BACKGROUND

1. Field of the Disclosure

The present disclosure relates to a surgical device and, more particularly, relates to a surgical tape for sealing a wound through which a surgical portal apparatus was placed to access a surgical site.

2. Description of the Related Art

Many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

Generally, in minimally invasive surgical procedures, surgical portal apparatus, such as trocars and cannulas, permit the introduction of a variety of surgical instruments into a body cavity or incision. A surgical portal apparatus is introduced through a cavity or incision to provide access to an underlying surgical site in the body. The incision is typically made using an obturator having a blunt or sharp radius within the passageway of the surgical portal apparatus. For example, a trocar has a cannula, a tube of rigid, thin wall construction, through which an obturator may be distally passed. The obturator is utilized to penetrate a body wall, such as an abdominal wall, or to introduce the surgical portal apparatus through the body wall, and is then removed from the surgical portal apparatus to permit introduction of surgical instrumentation utilized to perform the procedure therethrough.

Post-surgery, wound closure devices, such as sutures, are used to close the various layers of tissue (e.g., dermis, facias, muscle, peritoneum, etc.) of the formed wound. Suturing a patient after removal of a surgical portal apparatus may be cumbersome, while accumulating additional costs to the patient such as increased time spent in the operating room. For example, manual suturing may take approximately 2-4 minutes per surgical portal apparatus, with 4-8 surgical portal apparatus typically being utilized per procedure.

It would be desirable to provide a wound closure material that can quickly and easily effect closure of all tissue layers of a wound.

SUMMARY

A surgical tape applicator in accordance with the present disclosure includes a dispenser housing, a protective liner, and a surgical tape. The dispenser housing has a proximal end and a distal end and defines a passageway therethrough. The protective liner is disposed within the passageway of the housing. The surgical tape is at least partially disposed within the passageway and protected by the protective liner. The surgical tape has a first surface and a second surface each having at least one tissue reactive component.

Methods of using the surgical tape applicator are also described. In accordance with the present disclosure, a surgical tape applicator, as described above, may be introduced into a body cavity through a wound in tissue and then withdrawn to expose the surgical tape to the inner walls of the wound such that the wound is closed by bonding of the tissue reactive component of the first and second surfaces of the surgical tape with tissue.

BRIEF DESCRIPTION OF THE DRAWINGS

Embodiments of the present disclosure will be better appreciated by reference to the drawings wherein:

FIG. 1 is a perspective view of a surgical portal apparatus in the form of a seal housing and a portal sleeve which may be used in conjunction with a surgical tape applicator of the present disclosure;

FIG. 2 is a cross-sectional view of the surgical portal apparatus of FIG. 1;

FIG. 3A is a cross-sectional view of a surgical tape applicator in accordance with an embodiment of the present disclosure;

FIG. 3B is a cross-sectional view of a surgical tape applicator in accordance with another embodiment of the present disclosure;

FIG. 3C is a cross-sectional view of a surgical tape applicator in accordance with yet another embodiment of the present disclosure;

FIG. 4 is a cross-sectional schematic illustration of the surgical portal apparatus of FIGS. 1 and 2 positioned within tissue;

FIG. 6A is a perspective view, with parts separated, of a surgical tape applicator in accordance with another embodiment of the present disclosure;

FIG. 6B is a perspective view of the surgical tape applicator of FIG. 6B;

FIG. 7A is a perspective view of a surgical tape in accordance with an embodiment of the present disclosure;

FIG. 7B is a perspective view of the surgical tape of FIG. 7A in a folded configuration;

FIG. 7C is a perspective view of the surgical tape of FIG. 7A in an alternate folded configuration;

DETAILED DESCRIPTION

Figure 5A:
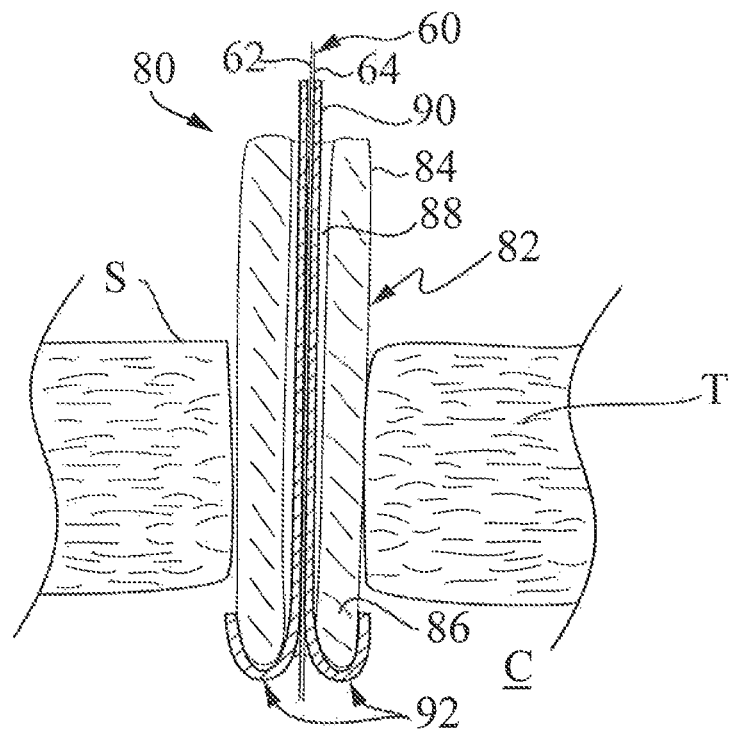
FIGS. 5A and 5B are cross-sectional schematic illustrations of the surgical tape applicator of FIG. 3A being positioned within tissue and removed from tissue, respectively, in accordance with an embodiment of the present disclosure.

Various exemplary embodiments of the present disclosure will be discussed hereinbelow in terms of a surgical tape applicator for use alone or in conjunction with a surgical portal apparatus during a surgical procedure. It should be understood that a surgical tape applicator of the present disclosure may be utilized after use of any of a variety of surgical portal apparatus that may be inserted into an incision in a variety of surgical applications. For example, the surgical portal apparatus may be, for example, a trocar, a cannula, an access port such as a SILS™ port, an introducer, among other surgical access devices within the purview of those skilled in the art.

The surgical tape applicator includes a surgical tape disposed within a dispenser housing. The surgical tape applicator may be placed within a wound through which a surgical portal apparatus was placed to access a surgical site, or the surgical tape applicator may be placed within a wound created by other means, such as a puncture wound, ulcer, or fistula, for example.

Embodiments of a surgical portal apparatus and a surgical tape applicator will now be described in detail with reference to the drawing figures wherein like reference numerals identify similar or identical elements. In the following discussion, the term "proximal" should be understood as referring to the portion of a structure that is closer to a clinician during proper use, and the term "distal" should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to the drawings, FIGS. 1 and 2 illustrate an embodiment of a surgical portal apparatus 10. Portal apparatus 10 includes a seal housing 20 mounted to a sleeve 30 that is configured and adapted for introduction through tissue into a body cavity of a patient.

Seal housing 20 includes a proximal end portion 22, a distal end portion 24, and a sidewall 26 connecting the proximal end portion 22 and the distal end portion 24. Proximal end portion 22 includes an aperture 28 aligned with a central housing axis "a" that is adapted for receiving surgical objects and instruments 12 of varying diameters therethrough. Examples of surgical objects and instruments which may be introduced through the surgical portal apparatus include clip appliers, graspers, dissectors, retractors, staplers, laser probes, photographic devices, endoscopes, laparoscopes, arthroscopes, tubes, electrosurgical cutting, coagulating, and ablation devices, and other tools within the purview of those skilled in the art.

The seal housing 20 may incorporate a seal 40 which, either alone or in combination with a valve 44, provides a substantial seal between a body cavity of a patient and the outside atmosphere before, during, and after insertion of a surgical instrument 12 through the surgical portal apparatus 10. A fluid tight interface is maintained via the seal 40 about the inserted surgical instrument 12. This substantially prevents gas and/or liquid leakage from the established surgical site so as to preserve the atmospheric integrity of a surgical procedure. Sidewall 26 may define one or more internal peripheral channels or recesses 27 for receiving a portion or component of the seal 40 and/or valve 44. Internal peripheral channel or recess 27 may be defined along any portion of the sidewall 26.

Seal 40 may be generally disc shaped and sized to fit within the seal housing 20. Seal 40 including an opening or slit 42 that is configured to form a fluid-tight fit about the surgical instrument 12. As illustrated in the current embodiment, the seal 40 is flat or planar. It is envisioned that the seal 40 may be any shape, such as having a tapered or funneled profile, for sealing and maintaining the integrity of the established surgical site. Seal 40 may be a gel seal, fabric seal, elastomeric seal, or combinations thereof.

Valve 44 may be placed distal, or internal to, the seal 40. Valve 44 may be a zero-closure valve such as a duck-bill valve having a slit 46 which is adapted to close in the absence of a surgical instrument 12 and/or in response to insufflation gases of the pressurized cavity. Further, valve 44 prevents fluids or debris from entering the seal housing 20 when the valve 44 is closed. Fluid pressure on the valve 44 will close the slit 46 thereby sealing the seal housing 20 from fluids. When a surgical object or instrument 12 is inserted through the valve 44, however, a seal is not always formed around the surgical instrument 12 thereby allowing some fluid to enter the seal housing 20 wherein the seal 40 prevent the fluid from exiting the seal housing 20. In the alternative, valve 44 may be a gel seal, balloon valve, or a flapper valve.

Distal end portion 24 of portal housing 20 including a joining member 25 for joining the seal housing 20 to the sleeve 30. Distal end portion 24 may be selectively releasably connectable to the sleeve 30 to cooperatively couple the seal housing 20 to the sleeve 30. Various means for releasably securing or connecting the seal housing 20 to the sleeve 30 are envisioned including a bayonet coupling, snap-fit, frictional fit, tongue and groove arrangement, threaded arrangement, cam-lock mechanisms or the like. As illustrated in the current embodiment, seal housing 20 is secured to the sleeve 30 via snap fit. Seal housing 20 may be mounted to the sleeve 30 before, during, or after, application of the sleeve 30 within the operative site. Alternatively, seal housing 20 may be permanently secured to the sleeve 30 by conventions means, such as, for example, ultrasonic welding, use of adhesives, or by monolithically forming the seal housing 20 with the sleeve 30.

Sleeve 30 may be any portal member suitable for the intended purpose of accessing a body cavity and defines a central longitudinal axis "b" extending along the length of the sleeve 30 from a proximal end 32 to a distal end 34. As illustrated, the central longitudinal axis "b" of the sleeve 30 may be coincident with the central housing axis "a" of the seal housing 20 when the seal housing 20 is mounted to the sleeve 30. Sleeve 30 further defines an internal longitudinal passageway 36 dimensioned to permit introduction and passage of a surgical instruments 12 therethrough. Sleeve 30 may be transparent, translucent, or opaque and may be formed of any suitable medical grade material, such as metal materials, like stainless steel, titanium, and aluminum; polymeric materials, like acrylonitrile-butadiene-styrene, polycarbonate, and polystyrene; and other rigid materials and combinations thereof as envisioned by one skilled in the art. Sleeve 30 may or may not include means for facilitating retention of the sleeve 30 within tissue. Such means include a plurality of locking elements, ribs, or other locking arrangements within the purview of those skilled in the art.

Turning now to FIG. 3, an embodiment of a surgical tape applicator 80 is illustrated. Surgical tape applicator 80 includes an elongated dispenser housing 82 having a substantially flat tubular shape. The housing 82 has a proximal end 84 and a distal end 86 and defines a passageway 88 therethrough. The housing 82 houses a surgical tape 60 protected by a protective liner 90. In embodiments, an outer wall of the housing 82 includes, or is covered by, a non-adherent absorbent material, such as gauze, to remove excess fluid from tissue in which the housing 82 is placed thereby wiping and/or drying the surrounding tissue prior to application of the surgical tape 60 thereto.

The protective liner 90 is affixed to the housing 82 at the distal end 86 of the housing 82. As illustrated, protective liner 90 is disposed within the passageway 88 of the housing 82 and is affixed solely at an outer wall 81 of the housing 82 to form liner tabs 92 at the distal end 86 thereof. In embodiments, the protective liner 90 may be affixed at both the proximal and distal ends 84, 86 of the housing 82 by liner tabs 91, 92, respectively, as illustrated in FIG. 3B, or solely at the proximal end 84 of the housing 82 as illustrated in FIG. 3C, provided that the protective liner 90 has a sufficient run length to facilitate removal of the surgical tape 60 therefrom.

While a surgical tape is illustrated and described in the current embodiment, it should be understood that the surgical tape may be any medical device that may be used for wound closure device such as, for example, meshes, scaffolds, soft tissue repair devices, grafts, slings, gauzes, buttresses, pledgets, wound dressings, drug delivery devices, tissue wraps, as well as other substrates, implants, composite materials, or combinations thereof.

Surgical tape 60 is fabricated from any biocompatible material. Surgical tape 60 may be a biodegradable and/or non-biodegradable material which may be natural or synthetic. The term "biodegradable" as used herein is defined to include both bioabsorbable and bioresorbable materials. By biodegradable, it is meant that the material decomposes, or loses structural integrity under body conditions (e.g., enzymatic degradation or hydrolysis), or is broken down (physically or chemically) under physiologic conditions in the body, such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof. Surgical tapes 60 utilizing biodegradable materials enable quick and complete wound healing to occur without permanently leaving a foreign material within tissue, while surgical tapes 60 fabricated from non-biodegradable materials provide continuous reinforcement and support to tissue.

Non-limiting examples of natural biodegradable polymers from which the surgical tape may be made include: proteins such as collagen, gelatin, albumin, serum, and casein; poly (amino acids); polysaccharides such as cellulose (including carboxymethyl cellulose), dextran, chitin, chitosan, alginate and hyaluronic acid; glycosaminoglycans; gut; as well as chemical derivatives thereof (substitutions and/or additions of chemical groups, for example, alkyl, alkylene, hydroxylations, oxidations, and other modifications routinely made by those skilled in the art), copolymers, and combinations thereof. Collagen as used herein includes natural collagen such as animal derived collagen, or synthetic collagen such as recombinant collagen. Additionally, natural materials include chemical modifications of the above-listed materials such as recombinant, aminated, sulfonated, and carboxylated polymer analogs.

Non-limiting examples of synthetic biodegradable polymers which may be utilized to form the surgical tape include polyhydroxy acids prepared from lactone monomers (such as glycolide, lactide, caprolactone, $\epsilon$-caprolactone, valerolactone, and $\delta$-valerolactone), carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include, for example: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-($\epsilon$-caprolactone-)); poly(glycolide-co-($\epsilon$-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; poly-ortho esters; and copolymers, block copolymers, homopolymers, blends, and combinations thereof.

Non-limiting examples of suitable nondegradable materials from which the surgical tape may be made include: polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

Surgical tape 60 may be porous, non-porous, or a combination thereof. In embodiments, the surgical tape 60 may be a film, foam, mesh, fibrous sheet, patch, or composite thereof including porous and/or non-porous layers of films, foams, and/or meshes. The term "porous" as used herein may define openings and spacings which are present as a surface characteristic or a bulk material property, partially or completely penetrating the surgical tape. Suitable materials for forming a porous substrate include, but are not limited to fibrous structures (e.g., knitted structures, woven structures, non-woven structures, etc.), foams (e.g., open or closed cell foams), and perforated films. Use of a porous substrate may allow for quicker healing through the openings formed therein.

In embodiments, the pores may be in sufficient number and size so as to interconnect across the entire thickness of the surgical tape. Woven fabrics, kitted fabrics, and open cell foam are illustrative examples of structures in which the pores can be in sufficient number and size so as to interconnect across the entire thickness of the substrate. In embodiments, the pores may not interconnect across the entire thickness of the substrate, but rather may be present at a portion thereof. Thus, in some embodiments, pores may be located on a portion of the surgical tape, with other portions of the surgical tape having a non-porous texture. Closed cell foam or fused non-woven materials are illustrative examples of structures in which the pores may not interconnect across the entire thickness of the substrate. Those skilled in the art reading the present disclosure will envision a variety of pore distribution patterns and configurations for the surgical tape.

Surgical tape 60 includes a first surface 62 and a second surface 64. The first and second surfaces 62, 64 of surgical tape 60 may include tissue reactive functional groups for fixation of the surgical tape 60 to tissue by crosslinking with reactive groups present in tissue "T" such as primary amine groups, secondary amine groups, hydroxyl groups, carboxylic groups, sulfonic groups, combinations thereof, and the like. Such groups include compounds possessing chemistries having some affinity for tissue.

For amine binding reactions, for example, isothiocyanates, isocyanates, acyl azides, N-hydroxysuccinimide (NHS) and sulfo-NHS esters, sulfonyl chlorides, aldehydes and glyoxals, epoxides and oxiranes, carbonates, arylating agents, imidoesters, carbodiimides, and anhydrides may be utilized. For carboxyl binding reactions, for example, diazoalkanes and diazoacetyl compounds may be utilized, as well as carbonyldiimidazoles, carbodiimides, and NHS, which convert carboxylic acid into a reactive intermediate which is susceptible to reaction with amines or alcohols. For hydroxyl binding reactions, for example, epoxides and oxiranes, carbonyldiimidazoles, disuccinimidyl carbonate and hydroxysuccinimidyl chloroformate, alkyl halogens, isocyanates, and methacryloyl or acryloyl chloride may be utilized, as well as oxidation with periodate or enzymatic oxidation. It is contemplated by the present disclosure that the functional groups may be the same or different at each occurrence. Thus, the surgical tape may have two or more different functional groups for bonding to tissue.

The term "bonding" as used herein refers to all types of chemical and physical crosslinking including covalent, ionic, and hydrophobic bonding. Chemical (covalent) crosslinking may be accomplished by any of a number of mechanisms, including free radical polymerization, condensation polymerization, anionic or cationic polymerization, step growth polymerization, electrophile-nucleophile reactions, combinations thereof, and the like. In addition, physical (non-covalent) crosslinks may result from complexation, hydrogen bonding, desolvation, Van der Waals interactions, ionic bonding, combinations thereof, and the like.

In embodiments, the reactive groups are electrophilic or nucleophilic groups capable of reacting with tissue and/or each other to form a bond. Electrophilic functional groups include, for example, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In embodiments, the electrophilic reactive group is a succinimidyl ester.

Suitable nucleophilic groups include, but are not limited to, —NH$_2$, —SH, —OH, —PH$_2$, —CO—NH—NH$_2$ and combinations thereof. In embodiments, the nucleophilic reactive group is an amine.

In other embodiments, bonding may be accomplished with biological cross-linking systems, including for example, antibody/antigen; biotin/avidin; complementary peptide binding sequences; nucleotide base pairing and cross-linking; lock and key protein binding chemistry; self-assembling peptides; combinations thereof, and the like. In embodiments utilizing biotin and avidin reactive chemistries, biotin may be functionalized to include reactive groups such as amine, sulfhydryl, carbonyl, and carboxy, based upon the substrate to which it is to be bound. Avidin, streptavidin, and their derivatives, may be utilized for bonding with a substrate containing biotin or with endogenous biotin within tissue.

The material forming the surgical tape 60 may be functionalized to provide reactive groups for binding or attaching to tissue. For example, amines may be provided on proteins, aminoglycans (such as chitosan, chondrotins, hyaluronic acid, and heparin), and polypeptides (like polylysine); carboxyl groups may be provided on proteins, polypeptides (like poly(glutamic acid)), polysaccharides (such as carboxylated dextran and carboxymethyl cellulose), and synthetic polymers (like carboxylated PEG and PEG-diadipate); hydroxyl groups may be provided on polysaccharides (like dextran), di-PEG adipate, and aliphatic polyesters (such as poly(lactic acid), poly(glycolic acid), poly(caprolactone), poly(trimethylene carbonate, poly(P-Dioxanone), and copolymers thereof); and thiols may be provided on some proteins. Alternatively, the surgical tape may be functionalized with tissue binding reactive groups, such as poly(lactic acid) and/or poly(glycolic acid), which include terminal carboxyl or hydroxyl groups.

The tissue reactive functional groups may be positioned on or near the first and second surfaces 62, 64 of surgical tape 60 using any suitable manner. For example, the surgical tape 60 may be formed from materials which naturally position reactive groups toward the outer surface of the surgical tape 60. In other examples, the surgical tape 60 may be surface-modified to covalently attach the reactive groups. In still other examples, the surgical tape 60 may be coated with an additional layer of material which includes the pendant reactive groups necessary to interact with the tissue as described herein.

Methods for coating the surgical tape 60 are within the purview of those skilled in the art, and include but are not limited to spraying, dipping, brushing, vapor deposition, coextrusion, capillary wicking, film casting, molding, and the like. The reactive groups may be combined with the surgical tape 60 in the form of a coating, film, foam, or powder on at least a portion of the first and second surfaces 62, 64, in embodiments, on the entirety of the first and second surfaces 62, 64 of the surgical tape 60.

In embodiments utilizing a coating, the coating process may include surface treatment of the surgical tape 60 in order to promote adhesion of the coating to the first and second surfaces 62, 64 of the surgical tape 60. The first and second surfaces 62, 64 of the surgical tape 60 can be treated using plasma, physical or chemical vapor deposition, pulsed laser ablation deposition, surface modification, or any other means within the purview of those skilled in the art to activate the first and second surfaces 62, 64. In other embodiments, treatment may include the use of a primer such as a cross-linkable compound. In yet other embodiments, one or more deposition treatments could be used alone or in conjunction with the primer to achieve the desired association of coating with the first and/or second surfaces 62, 64 of the surgical tape 60.

In embodiments, the first and/or second surfaces 62, 64 may be functionalized by attaching a reactive component thereto. Suitable reactive components may include crosslinkers, adhesives, sealants, couplers, and the like that are functionalized with at least one reactive group capable of bonding the first and second surfaces 62, 64 to tissue "T" as described above.

Examples of adhesive that may be utilized on the first and/or second surfaces 62, 64, of the surgical tape 60 include, for example, adhesives which cure upon tissue contact, which cure upon exposure to ultraviolet (UV) light, which are two-part systems which are kept isolated from one another and cure upon coming into contact with one another, or any other known suitable adhesive. Other examples of adhesives include silicones, acrylics, polyurethanes, polyesters, polyamides, and rubber-based adhesives. Yet other examples of adhesives which can be employed include protein derived, aldehyde-based adhesive materials, for example, the commercially available albumin glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively.

In embodiments, the protective liner 90 may be fabricated from collagen, dextran, or any other natural or synthetic material which will not react with the reactive groups on the surfaces 62, 64 of the surgical tape 60 to which it is applied. In some embodiments, the protective liner 90 may be coated with a non-stick material for ease of withdrawal of the surgical tape 60 therefrom. In other embodiments, the protective liner 90 may be fabricated from a non-stick material such as a silicone or fluorocarbon based material, like polytetrafluoroethylene (e.g., TEFLON).

To use the surgical portal apparatus 10 of the present disclosure in connection with the performance of a surgical task during a surgical procedure, the seal housing 20 is mounted to the sleeve 30 as discussed above. The surgical portal apparatus 10 is introduced into a body cavity "C" typically utilizing a sharp or non-bladed trocar obturator to access the body cavity "C" and the obturator is removed, placing the surgical portal apparatus 10 within wound "W" in tissue "T", as illustrated in FIG. 4. A surgical instrument 12 (FIG. 1) may then be advanced through the surgical portal apparatus 10 and into the body cavity "C". The desired surgical task is performed with the surgical instrument 12 (FIG. 1). Upon completion of use, the surgical portal apparatus 10 is removed from wound "W" and surgical tape applicator 80 may be placed within the wound "W" as illustrated in FIG. 5A.

Figure 5B:
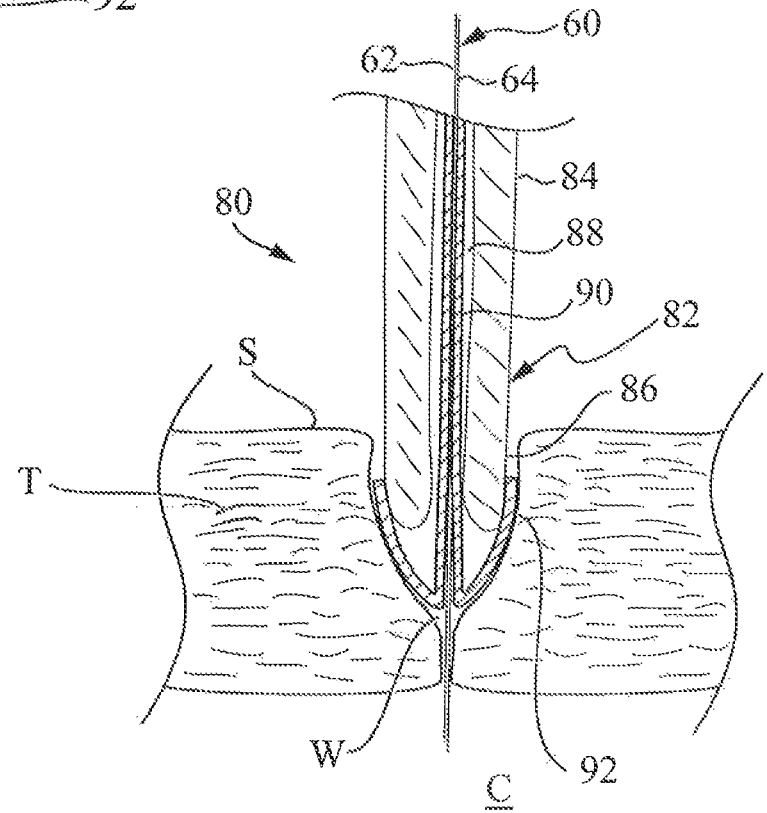

During placement of the surgical tape applicator 80 into wound "W", the housing 82 is passed through tissue "T" until the liner tabs 92 of the protective liner 90 enter the body cavity "C". The surgical tape 60 is protected during entry into the wound "W" by the protective liner 90 which is affixed to the distal end 86 of the housing 82. As the surgical tape applicator 80 is withdrawn from tissue "T", as shown in FIG. 5B, the distal end of the surgical tape 60 contacts the tissue "T" of wound "W" thereby securing the surgical tape 60 to tissue "T" as the protective lining 90 is inverted out of the distal end 86 of the housing 82. Continued withdrawal of the housing 82 strips the protective liner 90 from the surgical tape 60, exposing the surgical tape 60 to the inner walls of the wound "W". After the surgical tape applicator 80 is removed, the wound "W" is closed by bonding of the reactive components (e.g., tissue reactive functional groups or adhesives) disposed on the first and second surfaces 62, 64 of the surgical tape 60 with the tissue "T". Thereafter, the surgical tape 60 may be cut flush with the tissue surface "S". In embodiments, a vacuum (not shown) may be utilized to aid in the closure of tissue "T" and assist in sticking the surgical tape 60 to the tissue "T".

In embodiments, the protective liner may be fixed to a dispenser housing. As shown in FIGS. 6A and 6B, a surgical tape applicator 180 includes an elongated dispenser housing 182 having a proximal end 184 and a distal end 186, and defines a passageway 188 therethrough. A non-stick protective liner 190 is disposed within the housing 182 and is affixed to an outer wall 181 of the housing 182 at the distal end 186 by snap fit. It is envisioned that the protective liner 190 may be attached to the housing along any portion thereby by a variety of mechanical and chemical means within the purview of those skilled in the art. A surgical tape 160 is housed between two sides of the protective liner 190 disposed within the housing 182.

The surgical tape 160 includes an elongated body 170 defines a longitudinal axis "A" and includes a proximal end 172 and a distal end 174. The surgical tape 160 includes a plurality of pores 169 extending therethrough. The proximal end 172 of the surgical tape 160 extends proximally beyond the proximal end 184 of the housing 182 while the distal end 174 of the surgical tape 160 is disposed within, and protected by, the protective liner 190 and/or housing 182. Upon placement of the surgical tape applicator 180 into a wound, a clinician may push the proximal end 172 of the surgical tape 160 distally towards the housing 182, thereby moving the proximal end 172 of the surgical tape 160 into the housing 182 and the distal end 174 of the surgical tape 160 out of the distal end 186 of the housing 182. With the distal end 174 of the surgical tape 160 exposed to tissue, reactive components on the surfaces 162, 164 of the surgical tape 160 may bind with tissue "T". Accordingly, the elongated body 170 of the surgical tape 160 must be rigid enough to be pushed through the housing 182 of the surgical tape applicator 180, yet be flexible enough to maintain a seal with the tissue and accommodate movement of the tissue after placement therein. The housing 182 may then be withdrawn from the wound, leaving the surgical tape 160 in the tissue.

In embodiments, the protective liner 190 may be fabricated from, or coated with, a non-stick material as described above, or alternatively, a protective liner 190 may be omitted and the dispenser housing 182 may be fabricated from, or coated on an interior surface with, a non-stick material. In such embodiments, the proximal end 184 of the housing 182 may include an engagement structure to prevent the surgical tape 160 from inadvertently being deployed from the housing 182. For example, the proximal end 184 of the housing 182 may include a high friction surface, such as micro-texture (e.g., a plurality of fibers with a high packing density like gecko feet), for releasably engaging the proximal end 172 of the surgical tape 160. Alternatively, the proximal end 184 of the housing 182 may include a grooved surface so as to releasably retain the proximal end 172 of the surgical tape 160 to the housing 182, or the proximal end 184 of the housing 182 may include pinch tabs or other mechanical coupling means, like barbs, for temporarily securing the surgical tape 160 to the housing 182.

The distal end of a surgical tape may be biased to extend away from the longitudinal axis of the elongated body of the surgical tape to prevent the surgical tape from being pulled out of tissue during retraction of a surgical tape applicator. As illustrated in FIG. 7A, for example, a surgical tape 260 includes a flanged distal end 274 that is biased in an open, deployed position. The flanged distal end 274 may be collapsed or folded, as shown in FIG. 7B, to fit within a dispenser housing 182 (FIG. 8A) or the flanged distal end 274 may be hingedly connected to the elongated body 270 so that is may pivot with respect to the elongated body 270 from the deployed position of FIG. 7A to the folded position of FIG. 7C. Surgical tape 260 may be positioned within a housing in a similar manner as the surgical tape 160 of FIG. 6A, such that a proximal end 272 of the surgical tape 260 extends proximally from the proximal end 184 of the housing 182 and the folded distal end 274 is disposed within the housing 182.

Figure 8A:
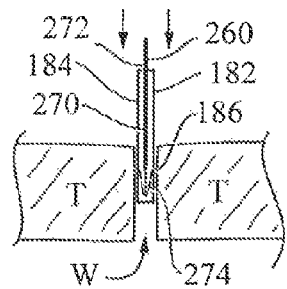
FIGS. 8A and 8B are cross-sectional schematic illustrations of a surgical tape applicator including the dispenser housing of FIGS. 6A and 6B and the surgical tape of FIG. 7A being positioned within tissue and the dispenser housing being removed from tissue, respectively, in accordance with an embodiment of the present disclosure.
Figure 8B:
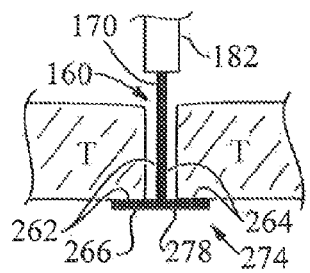
Figure 8C:
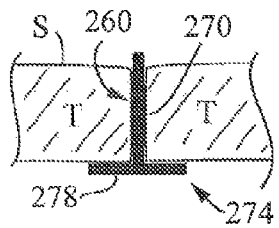
FIG. 8C is a cross-sectional schematic illustration of the surgical tape of FIGS. 8A and 8B positioned within tissue in accordance with an embodiment of the present disclosure.

In use, the surgical tape 260, disposed within housing 182, is placed within wound "W", as illustrated in FIG. 8A. Once fully inserted within wound "W", the proximal end 272 of the surgical tape 260 is pushed towards the proximal end 184 of the surgical housing 182 such that the distal end 274 of the surgical tape 270 is released from the distal end 186 of the housing 182. The distal end 274 of the surgical tape 260 then deploys into its biased open position, as illustrated in FIG. 8B, and the first and second surfaces 262, 264 bond with tissue "T". The surgical tape 260 is now prevented from being pulled out of the tissue "T" as the housing 182 is retracted. The wound "W" may then be closed by bonding of the first and second surfaces 262, 264 of the surgical tape 260 with the tissue "T", as illustrated in FIG. 8C. Thereafter, the surgical tape 260 may be cut flush with the tissue surface "S", or alternatively be adhered to the tissue surface "S", as shown in FIG. 9.

Figure 9:
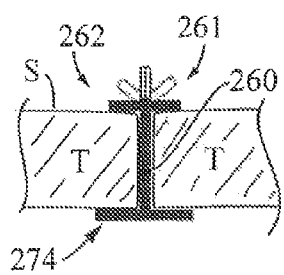
FIG. 9 is a cross-sectional schematic illustration of a surgical tape positioned within tissue in accordance with another embodiment of the present disclosure.

In some embodiments, such as that shown in FIG. 9, the proximal end 272 of the surgical tape 260 may include perforations 261 so that the surgical tape 260 may be bifurcated (shown in phantom). As illustrated, the surgical tape 260 extends from the wound "W" through the tissue surface "S" after placement in tissue "T". Rather than cutting the surgical tape 260 flush with the tissue surface "S", the proximal end 272 of the surgical tape 260 may be split and spread apart along perforations 261, in the direction of the arrows, to form its own bandage for closing the tissue surface "S".

A bottom surface 278 of the surgical tape 260 may include an anti-adhesive coating that acts as a barrier layer between the wound and the surrounding tissue to prevent the formation of adhesions. Alternatively, in embodiments in which the bottom surface of a surgical tape is anti-adhesive, the surgical tape may be placed in a wound "W" without the use of a dispenser housing.

Figure 10A:
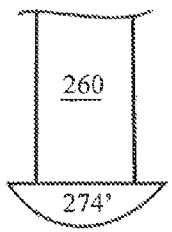
FIGS. 10A and 10B are front and side views of a surgical tape in accordance with an embodiment of the present disclosure.
Figure 10B:
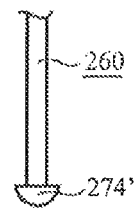
Figure 11:
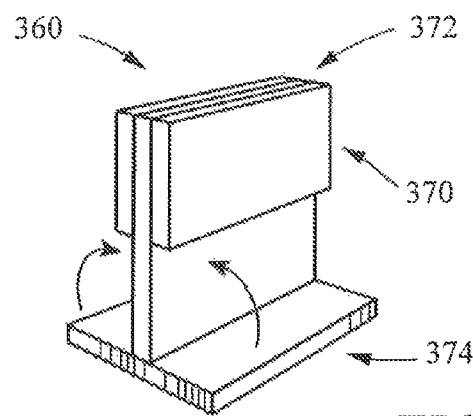
FIG. 11 is a perspective view of a surgical tape in accordance with another embodiment of the present disclosure.

While the flanged distal end 274 of the surgical tape 260 is illustrated above as being substantially flat, the flanged distal end 274' may also include some bulk and volume, as illustrated in FIGS. 10A and 10B. Alternatively, the surgical tape 360 may maintain a uniform profile when the distal end 374 is folded against the elongated body 370 in the direction of the arrows illustrated in FIG. 11. Rounded edges and/or a slim profile provide a surgical tape with an atraumatic distal end during insertion into tissue. While the surgical tape 360 is illustrated as a multi-layered structure, it is envisioned that the surgical tape may include a single, dual, or multi-layered construction.

Figure 12:
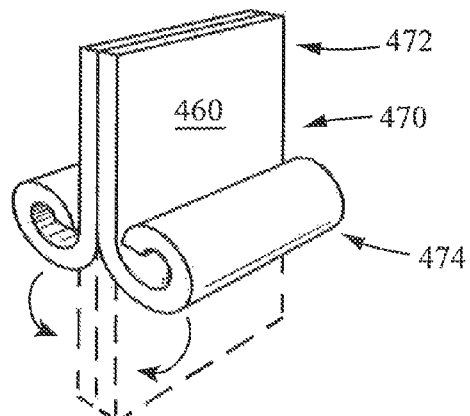
FIG. 12 is a perspective view of a surgical tape in accordance with yet another embodiment of the present disclosure.

As illustrated in FIG. 12, the distal end 474 may be biased in a rolled position and straightened (shown in phantom) for placement within a dispenser housing (not shown). When expelled from the distal end of a housing, the distal end 474 of the surgical tape 460 reverts back to its biased, rolled position. It is envisioned that the distal end 474 may include any of a variety of shapes that aid in the attachment of a surgical tape to tissue.

Figure 13:
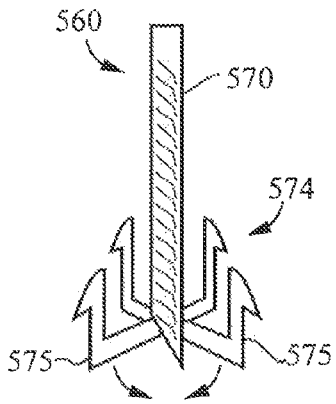
FIG. 13 is a perspective view of a surgical tape in accordance with an embodiment of the present disclosure.
Figure 14:
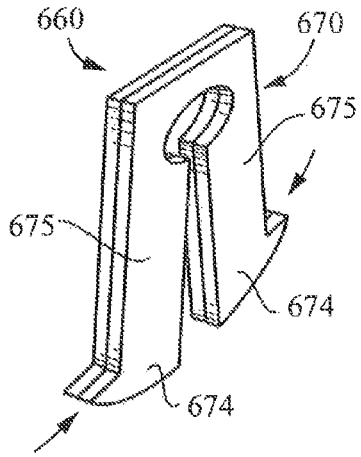
FIG. 14 is a perspective view of a surgical tape in accordance with another embodiment of the present disclosure.

In embodiments, a surgical tape may have a distal end including hooks, barbs, grips, or other mechanical attachment means for attachment to tissue. For example, as illustrated in FIG. 13, surgical tape 560 includes an elongated body 570 having a distal end 574 including barbed legs 575 pivotably connected to the elongated body 570. Barbed legs 575 are biased in an open, gripping position (as shown), such that the legs 575 are symmetrically spaced around the elongated body 570. The legs 575 may be pivoted in the direction of the arrows until they abut the elongated body 570 for placement within a dispenser housing (not shown). When the distal end 574 of the surgical tape 560 is release from a housing, the legs 575 returned to their open, biased position. In another embodiment, illustrated in FIG. 14, a surgical tape 660 includes two spaced resiliently flexible legs 675 that are springingly biased to extend outwardly from the longitudinal axis of the elongated body 670 of the surgical tape 660. Legs 675 may be squeezed together, in the direction of the arrows, during insertion into a dispenser housing (not shown). When the distal end 774 of the surgical tape 760 is extended past the distal end of a housing, the legs 675 return to their biased position and catch tissue, thereby preventing the surgical tape 660 from being pulled out of the tissue as the dispenser housing is retracted.

Figure 15:
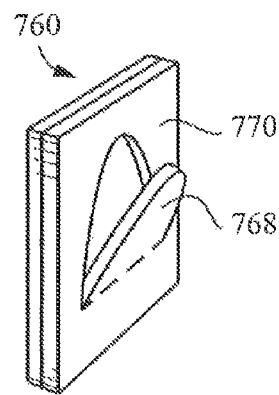
FIG. 15 is a perspective view of a surgical tape in accordance with yet another embodiment of the present disclosure.

It is also contemplated that other portions of a surgical tape may include sections that are biased to extend away from the longitudinal axis of the elongated body of the surgical tape to aid in the attachment of the surgical tape to tissue. As illustrated in FIG. 15, for example, a section of the elongate body 770 of a surgical tape 760 includes wings 768 which are biased to extend away from the elongated body 770 of the surgical tape 760.

Figure 16A:
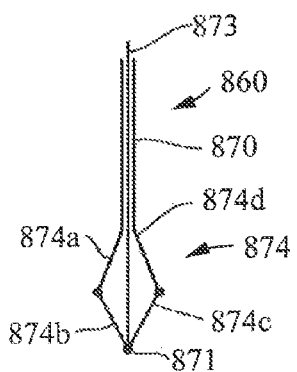
FIGS. 16A-16C are front, side, and end views of a surgical tape in accordance with an embodiment of the present disclosure.
Figure 16B:
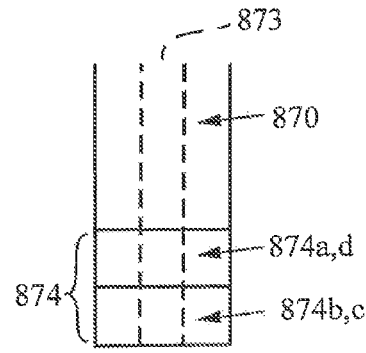
Figure 16C:
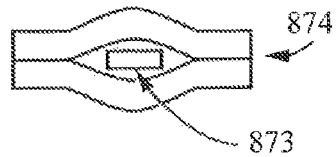
Figure 17A:
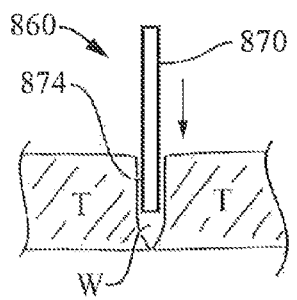
FIGS. 17A-17C are cross-sectional schematic illustrations of the surgical tape of FIGS. 16A-16C being positioned within tissue in accordance with an embodiment of the present disclosure.
Figure 17B:
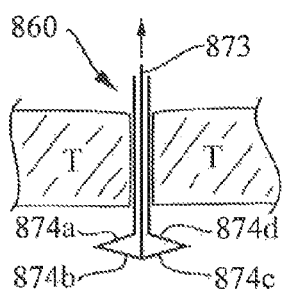
Figure 17C:
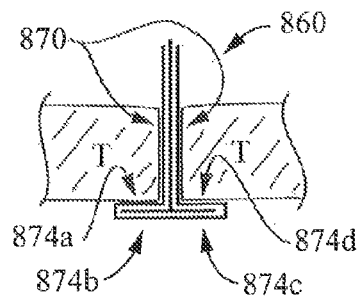

FIGS. 16A-16C illustrate another embodiment of a surgical tape 860. Surgical tape includes an elongated body 870 having a flexible distal end 874. Distal end 874 includes four hinged segments 874a-874d arranged in a diamond-like configuration. An elongated actuator 873 is connected to the distal end 874 at a distal-most hinge 871 located between segments 874b and 874c and extends through the length of the surgical tape 860 beyond the proximal end 872 of the elongated body 870. In embodiments, the elongated actuator 873 may be a suture, cord, or other biocompatible filament. The elongated body 870 of the surgical tape 860, as well as sections 874a and 874d includes reactive components as described above, for bonding to tissue while segments 874b and 874c may include an anti-adhesive coating. In use, as illustrate in FIG. 17A, the surgical tape 860 may be inserted into a wound "W". Once fully inserted, the elongated actuator 873 may be pulled proximally, as illustrated in FIG. 17B, to move segments 874b and 874c into abutment with sections 874a and 874d, respectively. As illustrated in FIG. 17C, the elongate body 870 and segments 874a and 874d bond to tissue "T", while segments 874b and 874c face away from the wound "W" and prevent adhesion of the surgical tape 860 to the surrounding tissue.

At least one bioactive agent may be combined with the surgical tape of the present disclosure. The term "bioactive agent", as used herein, is used in its broadest sense and includes any substance or mixture of substances that have clinical use. A bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the substrate in any suitable form of matter, e.g., films, powders, liquids, gels, combinations thereof, and the like.

The bioactive agent may be included on any portion of the surgical tape. The bioactive agents may be incorporated into the surgical tape during formation of the surgical tape, such as by free suspension, liposomal delivery, microspheres, microparticles etc., or by coating a surface of the surgical tape, or portion thereof, such as by polymer coating, dry coating, and freeze drying. In embodiments in which the surgical tape is porous, bioactive agents may be incorporated within the pores thereof.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used with the substrates of the present disclosure.

Other bioactive agents which may be included as a bioactive agent in the surgical tape of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; antiemetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Additional examples of suitable bioactive agents include viruses and cells; peptides; polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists and protein agonists; nucleic acids such as antisense molecules, DNA, and RNA; oligonucleotides; and ribozymes.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A surgical tape applicator, which comprises:
   a dispenser housing having a proximal end and a distal end and defining a passageway therethrough;
   a protective liner disposed within the passageway of the housing; and
   a surgical tape at least partially disposed within the dispenser housing and protected by the protective liner, the surgical tape including an elongated planar body defining a longitudinal axis and having first and second surfaces and proximal and distal ends, each of the first and second surfaces having at least one tissue reactive component, wherein a portion of the elongated planar body is biased in a first position extending away from the longitudinal axis of the elongated planar body, and movable to a second position aligned with the longitudinal axis of the elongated planar body.

2. The surgical tape applicator of claim 1, wherein the protective liner is affixed to the dispenser housing.

3. The surgical tape applicator of claim 1, wherein the protective liner is affixed solely at one of the proximal end and the distal end of the dispenser housing.

4. The surgical tape applicator of claim 1, wherein the protective liner is formed from, or coated with, a non-stick material.

5. The surgical tape applicator of claim 1, wherein the surgical tape is selected from the group consisting of films, foams, meshes, fibrous sheets, patches, and composite thereof.

6. The surgical tape applicator of claim 1, wherein the surgical tape is porous.

7. The surgical tape applicator of claim 1, wherein the surgical tape includes perforations.

8. The surgical tape applicator of claim 1, wherein the surgical tape includes wings on each of the first and second surfaces of the surgical tape, the wings being biased to extend away from the elongated body of the surgical tape.

9. The surgical tape applicator of claim 1, wherein the distal end of the surgical tape is biased to extend away from the longitudinal axis of the elongated body.

10. The surgical tape applicator of claim 9, wherein the distal end of the elongated body is hingedly connected to the elongated body.

11. The surgical tape applicator of claim 1, wherein the surgical tape includes a bottom surface having an anti-adhesive coating.

12. A method of closing a wound, the method comprising:
   introducing a surgical tape applicator into a body cavity of a wound in tissue, the surgical tape applicator including:
   a dispenser housing having a proximal end and a distal end and defining a passageway therethrough;
   a protective liner disposed within the passageway of the housing; and
   a surgical tape at least partially disposed within the dispenser housing and protected by the protective liner, the surgical tape including an elongated planar body defining a longitudinal axis and having first and second surfaces and proximal and distal ends, each of the first and second surfaces having at least one tissue reactive component, wherein a portion of the elongated planar body is biased in a first position extending away from the longitudinal axis of the elongated planar body, and movable to a second position aligned with the longitudinal axis of the elongated planar body; and withdrawing the surgical tape applicator to expose the surgical tape to inner walls of the wound, whereby the reactive component of the first and second surfaces of the surgical tape bond with tissue thereby closing the wound.

13. The method of claim 12, further comprising cutting the surgical tape at a tissue surface.

14. The method of claim 12, further comprising:

introducing a surgical portal apparatus into the body cavity;

performing surgical tasks through the surgical portal apparatus; and removing the surgical portal apparatus from the wound, prior to introducing the surgical tape applicator.

* * * * *